United States Patent [19]

Fürst et al.

[11] 4,312,812

[45] Jan. 26, 1982

[54] PROCESS FOR THE MANUFACTURE OF CHOLESTEROL DERIVATIVES

[75] Inventors: Andor Fürst, Basel; Ludwig Labler, Allschwil; Werner Meier, Bottmingen, all of Switzerland

[73] Assignee: Hoffmann-La Roche Inc., Nutley, N.J.

[21] Appl. No.: 226,293

[22] Filed: Jan. 19, 1981

[30] Foreign Application Priority Data

Feb. 12, 1980 [CH] Switzerland ........................ 1137/80

[51] Int. Cl.$^3$ ............................................... C07J 7/00
[52] U.S. Cl. ...................... 260/397.2; 260/239.55 R; 260/397.5
[58] Field of Search ..................................... 260/397.2

[56] References Cited

U.S. PATENT DOCUMENTS 3,822,254  7/1974  Partridge et al. ................ 260/397.2

OTHER PUBLICATIONS

Helvetica Chimica Acta 57 (1974) 764–771.
Helvetica Chimica Acta 60 (1977) 475–481.
J.C.S. Chem. Comm. (1975) 362–363.
J.C.S. Perkin I (1975) 2302–2307.
Chemical Abstracts 87 (1977) 168272k.
Chem. Pharm. Bull. 21 (1973) 457–458.
Chem. Pharm. Bull. 24 (1976) 825–828.

Primary Examiner—Elbert L. Roberts
Attorney, Agent, or Firm—Jon S. Saxe; Bernard S. Leon; James H. Callwood

[57]  ABSTRACT

The present disclosure is directed to a process for the preparation of cholesterol derivatives from corresponding 21-hydroxymethyl steroidal compounds.

8 Claims, No Drawings

PROCESS FOR THE MANUFACTURE OF CHOLESTEROL DERIVATIVES

DETAILED DESCRIPTION OF THE INVENTION

The present invention is directed to a process for the preparation of optionally-etherified 1α,25-dihydroxycholesterol. The invention is also concerned with intermediates obtainable according to this process.

The process provided by the invention comprises reacting a compound of the formula

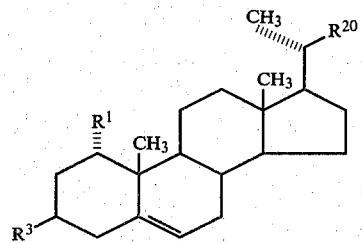

wherein $R^1$ and $R^3$ each is etherified hydroxy readily cleavable to hydroxy; and $R^{20}$ is hydroxymethylactivated by esterification, with a compound of the formula

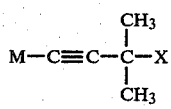

wherein M is sodium, potassium, lithium or magnesium/2; and X is OM or etherified hydroxy readily cleavable to hydroxy, and in the resulting compound of the formula

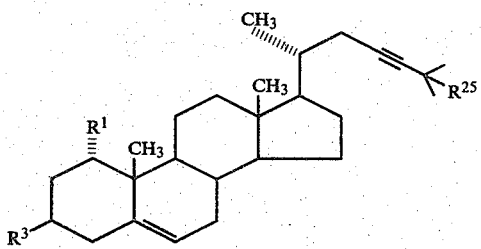

wherein $R^1$ and $R^3$ are as above; and $R^{25}$ is hydroxy or etherified hydroxy readily cleavable to hydroxy, in optional sequence hydrogenating the triple bond to a single bond and, if desired, hydrolyzing the etherified hydroxy groups $R^1$, $R^3$ and $R^{25}$ to hydroxy.

Ether groups $R^1$, $R^3$ and X which can be cleaved readily, i.e., without affecting other positions of the molecule, are preferably groups of the formula $R^5O-C(R^4, R^6)-O-$ in which $R^4$ is hydrogen or $C_{1-6}$-alkyl; and $R^5$ and $R^6$ each is $C_{1-6}$-alkyl or $R^5$ and $R^6$ together are $C_{3-6}$-alkylene. Especially-preferred ether groups are tetrahydropyran-2-yloxy, 1-ethoxyethoxy, methoxy-methoxy and 1-methoxy-1-methylethoxy.

Hydroxymethyl groups activated by esterification are preferably bromomethyl, iodomethyl, $C_{1-6}$-alkylsulphonyloxymethyl, especially mesyloxymethyl, or arylsulphonyloxymethyl such as phenylsulphonyloxymethyl optionally carrying one or more substituents selected from $C_{1-6}$-alkyl, fluorine, chlorine, iodine, nitro, cyano and trifluoromethyl, especially p-toluenesulphonyloxymethyl. The last-named group is especially preferred.

In the compounds of formula II, M preferably is lithium and X preferably is etherified hydroxy readily cleavable to hydroxy.

The reaction of a compound of formula I with a compound of formula II can be carried out in an aprotic inert solvent such as an ether, for example, dioxane or tetrahydrofuran, an amide, for example, diethylformamide, or dimethyl sulphoxide, preferably in dioxane or dimethyl sulphoxide. The reaction is conveniently carried out at an elevated temperature between about 40° C. and 150° C., preferably between 80° C. and 120° C., under argon.

For the conversion of a compound of formula III into 1α,25-dihydroxycholesterol, the hydrogenation of the triple bond in the 23,24-position and the hydrolysis of the ether groups $R^1$, $R^3$ and $R^{25}$ can be carried out in optional sequence.

The hydrogenation of the triple bond in the 23,24-position to a single bond can be carried out using a metal catalyst such as nickel, preferably Raney-nickel, platinum or palladium, conveniently in finely divided form and supported on an inert carrier such as carbon, calcium carbonate, barium carbonate or aluminum oxide. The hydrogenation is preferably carried out in a solvent such as an alcohol, for example, ethanol or methanol, an ester, for example, ethyl acetate, or an ether, for example dioxane or tetrahydrofuran, in the presence of a base such as an alkali metal carbonate, for example, sodium bicarbonate, or an amine, for example, pyridine, at about atmospheric pressure or at an elevated pressure and at a temperature of 0° C. to 100° C. The hydrogenation is preferably carried out in ethanol in the presence of sodium bicarbonate at atmospheric pressure and room temperature.

The hydrolysis of the ether groups in the 1-, 3- and 25-positions can be carried out with a strong acid such as a mineral acid, for example, hydrochloric acid, or a sulphonic acid, for example, p-toluenesulphonic acid, in aqueous medium containing a solvent such as an alcohol, for example, methanol, or an ether, for example, dioxane, at a temperature up to about 100° C., preferably with p-toluenesulphonic acid in methanol at room temperature.

The compounds of formulas I and II hereinbefore are known or can be prepared in analogy to known compounds.

The product of the process provided by the present invention, an optionally- etherified 1α,25-dihydroxycholesterol, is a known intermediate product in the preparation of the known vitamin $D_3$ metabolite 1α,25-dihydroxycholecalciferol.

The hydrogenation of a compound of formula III or of the product of its hydrolysis can also be carried out via a corresponding compound containing a cis- or trans-double bond in the 23,24-position. Thus, 1α,3β,25-trihydroxycholest-5-en-23-yne can be hydrogenated to 1α,3β,25-trihydroxycholest-5-ene via 1α,3β,25-trihydroxycholesta-5,23-(Z)-diene or 1α, 3β,25-trihydroxycholesta-5,23(E)-diene.

The hydrogenation to a compound containing a trans-double bond can be carried out with a complex metal hydride such as an alkali metal aluminium hydride, for example, lithium aluminium hydride, a mono- or di(lower alkoxy) alkali metal aluminium hydride, for example, lithium mono- or bis(t-butoxy)-aluminium hydride or sodium bis(2-methoxyethoxy)-aluminium hydride, in an inert organic solvent such as an ether, for example, dioxane, tetrahydrofuran or diethyl ether, at a temperature between 50° C. and 70° C., preferably with lithium aluminium hydride in tetrahydrofuran at about 70° C.

The hydrogenation to a compound containing a cis-double bond in the 23,24-position can be carried out in the presence of a catalyst such as nickel or a noble metal, for example, platinum, palladium or rhodium, optionally supported on a carrier such as carbon, calcium carbonate or aluminium oxide, in an inert solvent. There can also be used a partially deactivated catalyst comprising a noble metal, in free form or supported on a carrier, which is poisoned with a heavy metal and an aromatic nitrogen heterocycle, for example, a Lindlar catalyst comprising palladium on calcium carbonate which is poisoned with lead diacetate and quinoline. Examples of solvents which can be used are organic bases such as pyridine, esters such as ethyl acetate, ethers such as dioxane or alcohols such as ethanol. Pyridine is the preferred solvent. This hydrogenation is conveniently carried out at a hydrogen pressure between about 1 to 5 atmospheres, preferably at about 1 to 3, and at about 0° C. to 100° C., preferably at 0° C. to 50° C.

The hydrogenation of the double bond in the 23,24-position to a single bond can be carried out in the same manner as described earlier in connection with the complete saturation of the triple bond in an ether of formula III or the corresponding triol.

The compounds $1\alpha,3\beta,25$-trihydroxycholesta-5,23(E)-diene, $1\alpha,3\beta,25$-trihydroxycholesta-5,22(Z)-diene and $1\alpha,3\beta,25$-trihydroxycholest-5-en-23-yne are novel compounds and also form part of the present invention.

The following examples illustrate the present invention:

EXAMPLE 1

(A) The Preparation of the Starting Material 800 ml of tetrahydrofuran were treated at room temperature while stirring with 10.84 g (280 mmol) of lithium aluminium hydride. The suspension was cooled to −20° C. While cooling and stirring there was added dropwise under an argon atmosphere a solution of 26.5 g (46 mmol) of (20S)-1$\alpha$,3$\beta$-diacetoxy-20-methyl-21-(p-toluenesulphonyloxy)-pregn-5-ene in 450 ml of tetrahydrofuran. After 1.5 hours, 1.2 liters of tetrahydrofuran/ethyl acetate (1:1) were added to the suspension. The mixture was poured into 0.8 liters of stirred 2M potassium sodium tartrate solution (precooled to 0° C.), the organic solvents were removed, and the residue was extracted with 1.1 liters of ether. The ethereal extracts were washed with water and saturated sodium chloride solution and dried.

The resulting 24.1 g of (20S)-1$\alpha$,3$\beta$-dihydroxy-20-methyl-21-(p-toluenesulphonyloxy)-pregn-5-ene in 1.1 liters of benzene are concentrated to 500 ml, and the concentrate was treated with 8.27 g (97 mmol) of 3,4-dihydro-2H-pyran and 0.18 g (1.04 mmol) of p-toluenesulphonic acid. After 1.5 hours, the mixture was poured into 500 ml of saturated sodium hydrogen carbonate solution, 200 ml of ether were added thereto and, after shaking thoroughly, the organic phase was separated. The aqueous layer was washed with ether. The organic extracts were washed with saturated sodium chloride solution and dried. The residue was dissolved in ether and added to a column prepared with hexane/ether (9:1) and 1 kg of silica gel. Elution with hexane/ether mixtures gave 17.2 g of (20S)-20-methyl-1$\alpha$,3$\beta$-bis[(tetrahydro-2H-pyran-2-yl)oxy]-21-(p-toluenesulphonyloxy)-pregn-5-ene.

(B) The Process (a) A solution of 2.52 g (15 mmol) of 3-methyl-3-(tetrahydro-2H-pyran-2-yl)oxy-1-butyne in 50 ml of dioxane was treated dropwise at 6° C. with 7.5 ml of 2.0 M butyl lithium solution in hexane, and the mixture was stirred under argon at 6° C. for 2 hours and at 25° C. for 2 hours. The solution was treated with 3.35 g (5 mmol) of (20S)-20-methyl-1$\alpha$,3$\beta$-bis-[(tetrahydro-2H-pyran-2-yl)oxy]-21-(p-toluenesulphonyloxy)-pregn-5-ene, and the mixture was boiled under an argon atmosphere for 4 hours under reflux. The cooled mixture was poured into water and extracted with ether. The extract was washed with water, dried and evaporated. The residue gave, after chromatography on 100 g of silica gel with hexane/ether (9:1), 3.07 g (92%) of 1$\alpha$,3$\beta$,25-tris[(tetrahydro-2H-pyran-2-yl)oxyl]-cholest-5-en-23-yne; $[\alpha]_D^{25}=0°$ (C=0.5 in chloroform).

(b) A solution of 0.2 g (0.3 mmol) of 1$\alpha$,3$\beta$,25-tris[(tetrahydro-2H-pyran-2-yl)oxyl]-cholest-5-en-23-yne in 10 ml of ethanol was treated with 0.05 g of sodium hydrogen carbonate and 0.4 ml of concentrated ethanolic Raney-nickel suspension, and the mixture was shaken in a hydrogen atmosphere at normal pressure for 24 hours. The catalyst was filtered off, and the filtrate was evaporated. The residue, containing 1$\alpha$,3$\beta$,25-tris[(tetrahydro-2H-pyran-2-yl)oxy]-cholest-5-ene, was dissolved in 5 ml of methanol. 10 mg of p-toluenesulphonic acid monohydrate were added. The solution was left at room temperature for 3 hours. While stirring there were added dropwise 5 ml of water, the suspension was suction filtered, and the residue was dried. There was obtained 0.11 g (89%) of 1$\alpha$,3$\beta$,25-trihydroxy-cholest-5-ene which melts at 174°–176° C. after recrystallization from acetone.

(c) A solution of 1.0 g (1.5 mmol) of 1$\alpha$,3$\beta$,25-tris[(tetrahydro-2H-pyran-2-yl)oxyl]-cholest-5-en-23-yne in 14 ml of methanol was treated with 50 mg of p-toluenesulphonic acid monohydrate, and the mixture was left at room temperature for 1 hour. 16 ml of water was added dropwise while stirring. The separated material was filtered off under suction and dried. After chromatography on 60 g of silica gel with hexane/ether (1:1) and ethyl acetate, there was obtained 0.49 g (79%) of crystalline 1$\alpha$,3$\beta$,25-trihydroxy-cholest-5-en-23yne of melting point 204°–206° C. Recrystallization of a sample from acetone gave crystals of melting point 205°–206° C.; $[\alpha]_D^{25}=-12.6°$ (c=0.5 in methanol).

(d) A solution of 0.2 g (0.48 mmol) of 1$\alpha$,3$\beta$,25-trihydroxy-cholest-5-en-23-yne in 10 ml of ethanol was treated with 0.4 ml of concentrated ethanolic Raney-nickel suspension, and the mixture was shaken in a hydrogen atmosphere at normal pressure for 24 hours. The catalyst was filtered off, and the filtrate was evaporated. The crystalline residue, melting point 171°–172° C., gave, after recrystallization from acetone, 1$\alpha$,3$\beta$,25-trihydroxy-cholest-5-ene of melting point 174°–176° C.; $[\alpha]_D^{25}=-11.2°$ (c=0.5 in methanol).

(e) A solution of 1.0 g (2.4 mmol) of 1$\alpha$,3$\beta$,25-trihydroxy-cholest-5-en-23-yne in 100 ml of dioxane was treated with 1.0 g (26 mmol) of lithium aluminium hydride, and the mixture was boiled at reflux for 8 hours while stirring and gassing with argon. The mixture was left at room temperature for 16 hours. Within 10 minutes there were added dropwise 30 ml of dioxane/ethyl acetate (1:1) in such a manner that the temperature did not exceed 20° C. The suspension was poured into a mixture of 300 ml of 2M potassium sodium tartrate solution and 300 g of ice, and the mixture was freed from dioxane. The aqueous residue was extracted with ethyl acetate, the extract was washed with saturated sodium chloride solution, dried and evaporated. The crystalline residue was chromatographed on 100 g of silica gel. Elution with hexane/ether (1:1) initially gave 0.3 g of nonpolar material from which, by recrystallization from methanol, there was obtained $1\alpha,3\beta$-dihydroxy-cholesta-5-23,24-triene of melting point 132°–135° C.; $[\alpha]_D = -48.4°$ (c=0.5 in methanol). Subsequent elution with ethyl acetate yielded 0.70 g (70%) of $1\alpha,3\beta,25$-trihydroxy-cholesta-5-23(E)-diene. An analytical sample prepared by recrystallization from methanol melted at 195°–196° C.; $[\alpha]_D^{25} = -21.4°$ (c=1.0 in methanol).

(f) A prehydrogenated mixture of 0.30 g of 10% palladium on barium sulphate and 20 ml of pyridine was treated with 0.30 g (0.72 mmol) of $1\alpha,3\beta,25$-trihydroxy-cholest-5-en-23-yne, and the mixture was shaken in a hydrogen atmosphere at normal pressure. After completion of the hydrogenation (1.45 hours), the mixture was concentrated, the residue was treated with methylene chloride and suction filtered. The filtrate was washed with 1 N hydrochloric acid, saturated sodium hydrogen carbonate solution and water, dried and evaporated. The residue was chromatographed on 10 g of silica gel with benzene/ethyl acetate (1:1). There was obtained 0.30 g of $1\alpha,3\beta,25$-trihydroxy-cholesta-5,23(Z)-diene of melting point 146°–147° C. Recrystallization from ether gave crystals of melting point 150°–151° C.; $[\alpha]_D^{25} = -26.6°$ (c=1.0 in methanol).

(g) A solution of 0.136 g (0.32 mmol) of $1\alpha,3\beta,25$-trihydroxy-cholesta-5,23(E)-diene in 18 ml of ethanol was treated with 0.2 ml of concentrated ethanolic Raney-nickel suspension, and the mixture was shaken in a hydrogen atmosphere at normal pressure for 24 hours. After filtration and evaporation of the filtrate, there was obtained 0.136 g of $1\alpha,3\beta,25$-trihydroxy-cholest-5-ene of melting point 170°–174° C. After recrystallization from acetone, the product melted at 174°–176° C. and was identical with the product obtained in paragraph (b).

(h) A solution of 0.136 g (0.32 mmol) of $1\alpha,3\beta,25$-trihydroxy-cholesta-5,23(Z)-diene in 18 ml of ethanol was treated with 0.2 ml of concentrated ethanolic Raney-nickel suspension, and the mixture was shaken in a hydrogen atmosphere at normal pressure for 24 hours. After filtration and evaporation of the filtrate, there was obtained 0.135 g of $1\alpha,3\beta,25$-trihydroxy-cholest-5-ene of melting point 171°–175° C. After recrystallization from acetone, the product melted at 174°–176° C. and is identical with the product obtained in paragraph (b).

EXAMPLE 2

(A) The Preparation of the Starting Material (a) 59.0 g (100 mmol) of (20S)-$1\alpha,3\beta$-dihydroxy-20-methyl-21-(p-toluenesulphonyloxy)-pregn-5-ene in 2.5 liters of toluene were treated at room temperature with 0.25 g (0.68 mmol) of p-toluenesulphonic acid and 30.12 g (0.4 mol) of ethyl vinyl ether. After 30 minutes at room temperature, 15.0 ml of triethylamine were added. The mixture was evaporated, and the residue was dried. There were obtained 67.0 g of (20S)-$1\alpha,3\beta$-bis(1-ethoxyethoxy)-20-methyl-21-(p-toluenesulphonyloxy)-pregn-5-ene.

(b) 129.1 g (1.5 mol) of 3-hydroxy-3-methyl-but-1-yne and 0.38 g of p-toluenesulphonic acid were treated dropwise at 4° C. while stirring with 112.95 g (1.5 mol) of ethyl vinyl ether. Then 7.5 ml of triethylamine were added, and the mixture was distilled in vacuo. There were thus obtained 143.0 g (60%) of 3-(1-ethoxyethoxy)-3-methyl-but-1-yne of boiling point 43° C./15 Torr.

(B) The Process (a) A stirred solution, cooled to 9° C., of 46.8 g (0.3 mol) of 3-(1-ethoxyethoxy)-3-methyl-but-1-yne in 1.0 liters of dioxane was treated dropwise under argon with 150 ml (0.3 mol) of 2M n-butyl lithium in hexane. The solution was stirred at 7°–9° C. for 2 hours and at room temperature for 2 hours. Thereafter, there was added to the mixture a solution of 67.0 g of (20S)-$1\alpha,3\beta$-bis(1-ethoxyethoxy)-20-methyl-21-(p-toluenesulphonyloxy)-pregn-5-ene in 0.4 liters of dioxane and, while stirring, solvent was distilled off until the internal temperature was 93° C. The mixture was then stirred at 100° C. under argon for 64 hours. After cooling, carbon dioxide was conducted into the mixture. The mixture was poured into ice water, and the emulsion was extracted with ether. The extracts were washed with saturated sodium chloride solution, dried and evaporated. There were obtained 73.6 g of crude $1\alpha,3\beta,25$-tris(1-ethoxyethoxy)-cholest-5-en-23-yne.

(b) 120 ml of a concentrated suspension of Raney-nickel in 2.1 liters of ethanol was stirred in a hydrogen atmosphere for 24 hours at room temperature and normal pressure, 0.29 liters of hydrogen being absorbed. After the addition of 21.0 g of sodium hydrogen carbonate and a solution of 73.6 g of $1\alpha,3\beta,25$-tris(1-ethoxyethoxy)-cholest-5-en-23-yne in 1.0 liters of ethanol, the mixture was stirred in a hydrogen atmosphere for 24 hours at room temperature and normal pressure, 4.63 liters of hydrogen being taken up. The suspension was filtered, the residue was washed with ethanol, and the filtrate was evaporated and dried. There was obtained 71.6 g of crude $1\alpha,3\beta,25$-tris(1-ethoxyethoxy)-cholest-5-ene.

(c) A solution of 36.2 g of $1\alpha,3\beta,25$-tris(1-ethoxyethoxy)-cholest-5-ene in 0.75 liters of methanol was treated with 5.6 g (29 mmol) of p-toluenesulphonic acid monohydrate, and the mixture was stirred at room temperature for 45 minutes. 1.8 liters of water was dropped into the solution. The suspension was suction filtered, and the residue was washed neutral with water and dried. There was obtained 21.3 g of $1\alpha,3\beta,25$-trihydroxycholest-5-ene which melted at 172°–175° C. after recrystallization from acetone.

What is claimed is:

1. A process for the preparation of optionally-etherified $1\alpha,25$-dihydroxycholesterol, which process comprises reacting a compound of the formula

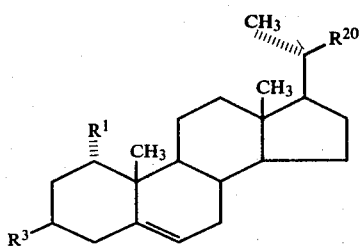

wherein $R^1$ and $R^3$ each is etherified hydroxy readily cleavable to hydroxy; and $R^{20}$ is hydroxymethyl activated by esterification,
with a compound of the formula

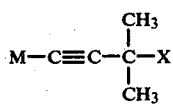

wherein M is sodium, potassium, lithium or magnesium/2; and X is OM or etherified hydroxy readily cleavable to hydroxy, and in the resulting compound of the formula

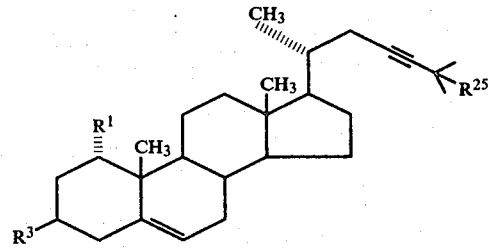

wherein $R^1$ and $R^3$ are as above; and $R^{25}$ is hydroxy or etherified hydroxy readily cleavable to the hydroxy group, if desired, hydrolyzing said etherified hydroxy groups $R^1$-, $R^3$- and $R^5$- contained in the compound of formula III and reacting said compound of formula III or the product of its hydrolysis with a hydrogenation agent.

2. A process according to claim 1 wherein said hydrogenation is carried out either using a complex metal hydride so that the triple bond contained in said compound of formula III or in the product of its hydrolysis is converted to a trans-double bond, or using a metal catalyst so that said triple bond is converted to a cis-double bond, and hydrogenating said trans-or cis-double bond to a single bond using a metal catalyst in the presence of a base.

3. A process according to claim 1 or claim 2 wherein there are used as the starting materials compounds of formulas I and II in which $R^1$, $R^3$ and X are etherified hydroxy of the formula $R^5O-C(R^4,R^6)-O-$ wherein $R^4$ is hydrogen or a $C_{1-6}$-alkyl; and $R^5$ and $R^6$ each is a $C_{1-6}$-alkyl or $R^5$ and $R^6$ together are $C_{3-6}$-alkylene; and in which $R^{20}$ is arylsulphonyloxymethyl or $C_{1-6}$-alkylsulphonyloxymethyl.

4. A process according to claim 3 wherein there are used as the starting materials compounds of formula I and II in which $R^1$, $R^3$ and X are 1-ethoxyethoxy or 2-tetrahydropyranyloxy; $R^{20}$ is p-toluenesulphonyloxymethyl; and M is lithium.

5. Compounds of the formula

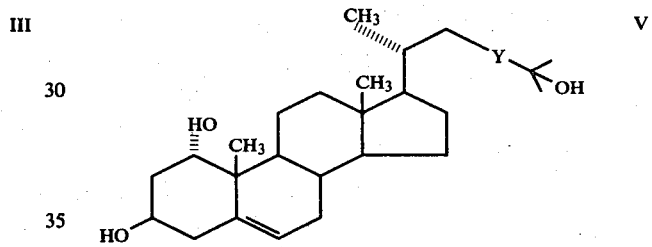

wherein Y is $-C\equiv C-$ or cis- or trans-$-CH=CH-$.

6. 1α,3β,25-trihydroxycholest-5-en-23dyne.
7. 1α,3β,25-trihydroxycholesta-5,23(E)-diene.
8. 1α,3β,25-trihydroxycholesta-5,23(Z)-diene.

* * * * *